US00PP28785P2

(12) United States Plant Patent
Hansen

(10) Patent No.: US PP28,785 P2
(45) Date of Patent: Dec. 19, 2017

(54) ***HOSTA* PLANT NAMED 'ANGEL FALLS'**

(50) Latin Name: ***Hosta* hybrid (Tratt.)**
Varietal Denomination: Angel Falls

(71) Applicant: Hans A. Hansen, Zeeland, MI (US)

(72) Inventor: Hans A. Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 14/999,733

(22) Filed: Jun. 21, 2016

(51) Int. Cl.
*A01H 5/12* (2006.01)

(52) U.S. Cl.
USPC ..... Plt./353

(58) Field of Classification Search
USPC ..... Plt./353
CPC ..... A01H 5/0272; A01H 5/02; A01H 5/12; A01H 5/00
See application file for complete search history.

(56) References Cited

PUBLICATIONS

American *Hosta* Society Online Auction Results p. 2015 retrieved on Jul. 24, 2017, retrieved from the Internet at <http://www.americanhostasociety.org/Activities/ahsresults15.htm> pp. 1-4.*
American *Hosta* Society 2015 Big Bid Items retrieved on Jul. 24, 2017, retrieved from the Internet at <http://www.americanhostasociety.org/Activities/15onlineBigBidPlants.htm> pp. 1-5.*
Cox's Plant Farm 2016 Spring Catalog retrieved on Jul. 24, 2017, retrieved from the Internet at <file:///C:/Users/jhwu/Downloads/Cox's%20Plant%20Farm%20-%202016-Catalog.pdf> pp. 1, 6-7.*

* cited by examiner

*Primary Examiner* — June Hwu

(57) ABSTRACT

The new and distinct *Hosta* plant named *Hosta* 'Angel Falls' with arching, elongated, cordate leaves having dark green margins with wide yellowish centers that develop into a creamy-white to near white centers. Flowers are light lavender on large-sized plant held attractively above the variegated foliage; each flower subtended and set off by large pointed bract.

2 Drawing Sheets

Latin botanical classification: *Hosta* hybrid (Tratt.).
Variety denomination: 'Angel Falls'.

BACKGROUND OF THE PLANT

The present invention relates to the new and distinct *hosta* plant, *Hosta* 'Angel Falls' discovered by Hans A. Hansen on spring of 2010 in a greenhouse at a wholesale perennial nursery in Zeeland, Mich., USA. The plant was found as an un-induced whole plant mutation of the *Hosta* cultivar 'Niagara Falls' (not patented). 'Angel Falls' can best be described as a reverse color pattern mutation from 'Bridal Falls' U.S. Plant Pat. No. 25,594 where the leaf variegation has switched positions.

The most similar known *hosta* cultivars are: 'American Hero' U.S. Plant Pat. No. 23,587, 'Bridal Falls' U.S. Plant Pat. No. 25,594, 'Cyclone' (not patented), 'Greenhead Center Court' (not patented), 'Niagara Falls' (not patented), 'Satin Doll' (not patented), 'The Queen' (not patented), and 'Guardian Angel' (not patented).

Compared to the sport parent, *Hosta* 'Niagara Falls', the new plant, is smaller in habit and has leaves with that emerge with creamy yellow centers that develop to a creamy white to near white and sinuate or undulate margins of dark green margins. The flower scape generally greyed-yellow colored on the new plant rather than olive green. Compared to 'American Hero' the new plant has more arching foliage with stronger sinuate to undulate leaf margins. 'Satin Doll' has similar shaped foliage, but the margin is not as sinuate to undulate as in 'Angel Falls'. Compared to 'Guardian Angel' the new plant has foliage that is more sinuate to undulate, and the center leaf color of 'Guardian Angel' is viridescent rather than albescent. 'Cyclone' is a smaller plant, has smaller leaves with leaf centers that are more white in the spring, and without the arching habit and lacks the sinuate to undulate margin. The new plant is larger in both height and width than 'Greenhead Center Court' and also has a more cordate leaf base and more sinuate to undulate margin. 'The Queen' is smaller in habit, has flowers that are deeper lavender, stiffer more upright foliage and less sinuate to undulate margins.

No plants of *Hosta* 'Angel Falls' have been sold, in this country or anywhere in the world, prior to the filing of this application, nor has any disclosure of the new plant been made prior to the filing of this application with the except that which was disclosed within one year of the filing of this application and was either derived directly or indirectly from the inventor.

'Angel Falls' has not been observed under all possible environments. The phenotype may vary slightly with different environmental conditions, such as temperature, light, fertility, moisture and maturity levels, but without any change in the genotype.

The new plant has been successfully propagated by division of the rhizome at a wholesale perennial nursery in Zeeland, Mich., USA and also by tissue culture methods and found to produce identical plants that maintain the unique characteristics of the original plant. The plant is stable and reproduces identical, true to type individuals in successive generations of asexual reproduction.

BRIEF SUMMARY OF THE PLANT

There are over 5,400 cultivars registered with The American *Hosta* Society, which is the International Cultivar Registration Authority for the genus *Hosta* and a similar number of unregistered cultivars. *Hosta* 'Angel Falls' differs from all these registered and unregistered cultivars known to the inventor in the following combined traits:

1. Plant of moderate size with foliage that arches over in maturity.
2. Elongated cordate foliage that emerges with yellowish centers and develops to a creamy-white to near-white with sinuate margins of dark green margins.
3. Foliage has deeply impressed veins above and sharply costate below.
4. Numerous light-lavender slightly pendulous flowers on erect scapes well above foliage with large bracts below each flower.

BRIEF DESCRIPTION OF THE DRAWINGS

The photographs of the five-year-old plant demonstrate the overall appearance of the plant, including the unique traits, grown in a partially shaded greenhouse in Zeeland, Mich. The colors are as accurate as reasonably possible with color reproductions. Ambient light spectrum, source, direction and temperature may cause the appearance of minor variation in color.

DETAILED BOTANICAL DESCRIPTION

Figure 1:
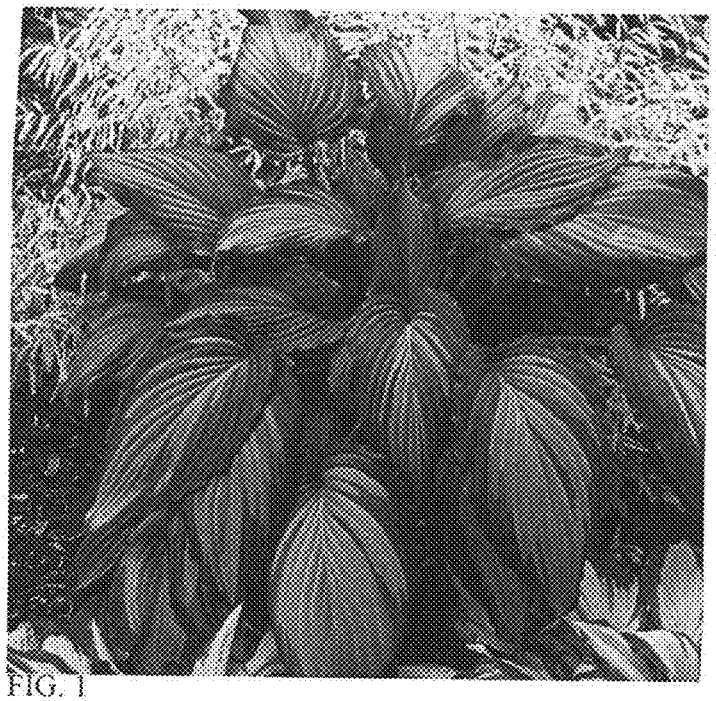
FIG. 1 shows a multi-division clump of a five-year-old plant in mid-season.
Figure 2:
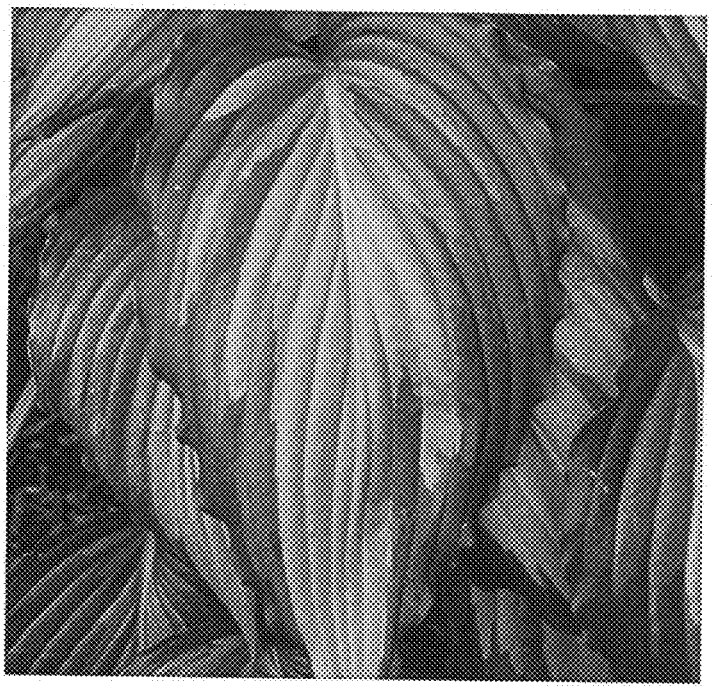
FIG. 2 shows a close-up of a leaf with variegation and sinuate margin.
Figure 3:
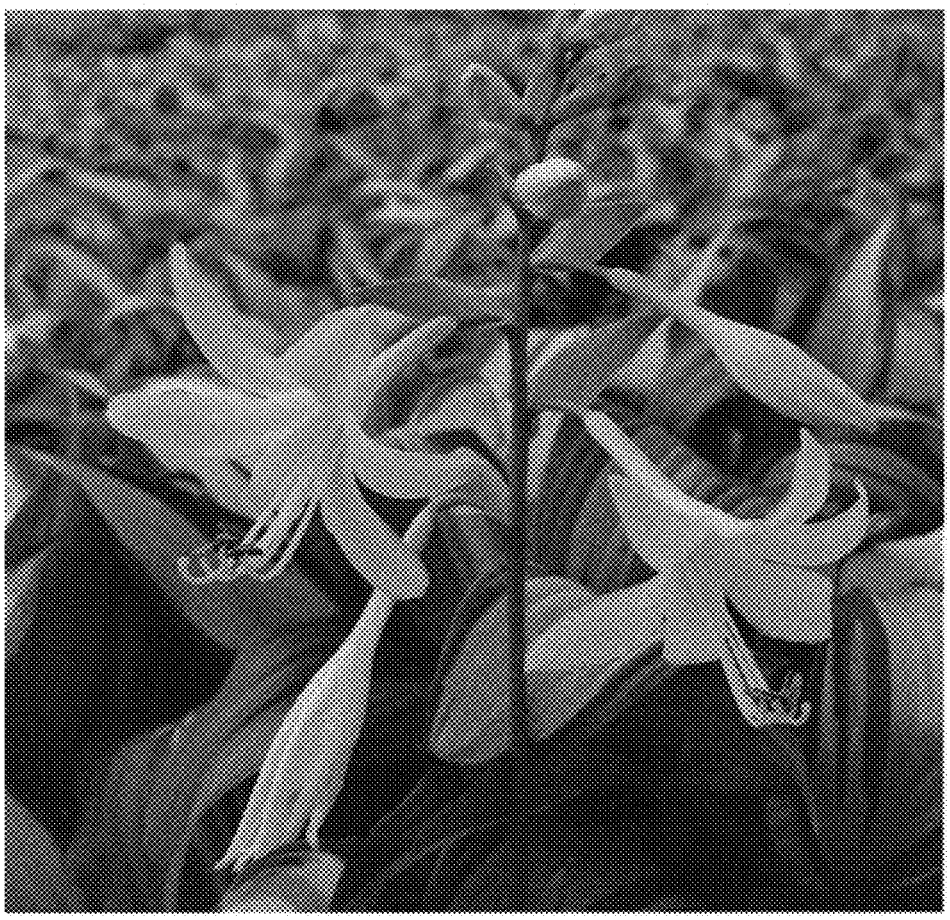
FIG. 3 shows a close-up of the flowers of six-month-old plants with less mature foliage but later in the season.

The following descriptions and color references are based on the 2001 edition of The Royal Horticultural Society Colour Chart except where common dictionary terms are used. The new plant, *Hosta* 'Bridal Falls', has not been observed under all possible environments. The phenotype may vary slightly with different environmental conditions, such as temperature, light, fertility, growth rate, moisture and specimen maturity, but without any change in the genotype. One skilled in the art would recognize the phenotype of the new plant would differ based on maturity level or number of years without dividing. The following observations and size descriptions are of a five-year-old plant in a greenhouse in Zeeland, Mich. with white plastic glazing and light fertilizer.

Botanical classification: *Hosta* hybrid.

Mutation parentage: *Hosta* 'Niagara Falls' (not patented).

Propagation method: By sterile laboratory tissue culture propagation and garden division.

Growth rate: Moderate.

Crop time: Under normal winter and spring growing conditions about 24 to 27 weeks to finish from a from rooted tissue culture liner to a 65 mm pot.

Time to initiate roots from tissue culture: About three weeks.

Plant description:

Plant shape and habit: Hardy, long-lived, herbaceous perennial, densely rhizomatous, forming a large mounded clump in maturity, with basal rosette of arching leaves on long petioles; usually radially symmetrical.

Roots: Normal, fleshy, lightly branching, cream-colored in normal soil.

Plant size: Foliage height about 50 cm tall; width of plant at the widest point is approximately 90 cm at the widest point just above soil line; about 15 divisions.

Foliage description:

Leaf blade: Cordate; entire sinuate margins; cordate leaf base with acute to acuminate apex; flat, mostly bilaterally symmetrical, with deeply impressed adaxial veins and ribbed abaxial; glabrous adaxial and abaxial; adaxial surface slightly glaucous becoming dull matte-surfaced late in growing season, abaxial surface moderately glaucous remaining throughout growing season; margin variegation width portion increasing with maturity from year to year; width of variegation irregular with jetting of intermediate portion, to about 4.2 cm, average of about 2.5 cm; length to width ratio of about 1.5:1.0; to about 33.5 cm long and 20.0 cm across, average about 27.5 cm long and 15.5 cm wide; 13 to 14 pairs of major parallel veins and one main center vein.

Blade color: Early season as emerging adaxial center more yellow than RHS 145D and more green than RHS 160B, adaxial margin between RHS 138A and RHS 138B, intermediate colors of RHS 145B, nearest RHS 138D and nearest RHS 144D in small irregular and linear patches between the margin and center; early season as emerging abaxial center more green than RHS 11B and more yellow than RHS 162D, abaxial margin more yellow than RHS 138A and more green than RHS 147B, intermediate colors of nearest RHS 145C and nearest RHS 148D in large irregular and linear patches between the margin and center; mid-season and later adaxial margin nearest RHS 137A, creamy-white center lighter than RHS 155D, large and small irregular intermediate patches of nearest RHS 147D and other smaller intermediate patches of nearest RHS 145D, lighter and greener than RHS 148C and lighter than RHS 153D; mid-season and later abaxial margin nearest RHS N138B, creamy centers lighter than RHS 155D and large and small irregular intermediate patches or striations of nearest RHS 145A, RHS N144A, RHS 151C and RHS 154D.

Veins: 13 to 14 pairs of major parallel veins, with midrib; veins impressed to a depth of about 3.0 mm above and ridged below.

Vein color: On early season adaxial margin nearest RHS 138A, and center nearest RHS 145C; abaxial margin and center the same color as the surrounding leaf tissue.

Petioles: Entire, concavo-convex, glabrous, glaucous, upright to arching; to about 39.5 cm long and about 1.8 cm wide, average about 35.5 cm long and about 1.2 cm wide measured at about 3 cm above soil line.

Petiole color: Adaxial and abaxial margin between RHS 138C and RHS 138B, and lighter than RHS 155D in the adaxial and abaxial center.

Flower description:

*Buds*.—Clavate; bluntly acute to rounded apex with longer thin base; one day prior to opening about 6.5 cm long and 1.7 cm wide at the broadest portion.

*Bud color*.—Lighter than RHS 85D at proximal fused base and lighter still to near white with very slight tinting of RHS 85D at the distal end.

*Flowers*.—Closely arranged, 20 to 28 per scape; each subtended by bract; funnelform; about 5.4 cm wide and 6.8 cm long, (distal flowers slightly smaller); remain open for a normal period, usually one day on or cut from plant; scapes remain effective from late-June into mid-July in Zeeland, Mich.

*Flower fragrance*.—No detectable fragrance.

*Tepals*.—Two sets of three fused in the basal two thirds; acute apex; margins entire; glabrous, approximately 6.8 cm long and 1.4 cm wide.

*Tepal color*.—Abaxial tepal color lighter than RHS 85D; abaxial corolla tube portion nearest mixture of RHS 192D and lighter than RHS 85D; adaxial tepal center middle portion nearest RHS 84C with adaxial margins near white, lighter than RHS N155D in outer 1.0 to 2.0 mm; inner tepals with clear transparent edge of about 1.0 mm wide.

Gynoecium: Single.

*Style*.—About 7.3 cm long, 1 mm diameter, curled slightly upward in the distal 1.5 mm; color white, lighter than RHS 155D the with basal 1.5 mm nearest RHS 145D.

*Stigma*.—Globose; 1 mm to 2 mm in diameter, color lighter than RHS 155D.

*Ovary*.—Oval, about 6 mm long and 3 mm diameter; between RHS 145A and RHS 145B.

Androecium: Six.

*Filaments*.—Six, about 6.9 cm long and 1.0 mm in diameter; with slight curve upward in proximal 1.5 mm; color lighter than RHS 11D.

*Anthers*.—Oblong; dorsifixed; versatile, longitudinal; about 4.0 mm long and 1.5 mm wide, color nearest RHS 11C.

*Pollen*.—Elliptical, less than 0.1 mm long, color nearest RHS 13B.

Bracts: Subtending each flower, lanceolate, margins entire, glaucous, glabrous, concavo-convex, widest at middle and gradually tapering to acute apex and sessile clasping base; size of lowest bract about 6.4 cm long and 1.5 cm wide before first flower, progressively decreasing in both length and width; drying as flowers open.

Bract color: Adaxial and abaxial margins nearest RHS 146B with slight tinting of nearest RHS N186B; adaxial blend between RHS 145B, RHS 145C and RHS 160A, abaxial center nearest RHS 145D; after flower drop and before drying developing to nearest RHS N144D.

Pedicel: Terete, glaucous, glabrous; about 10.0 mm long and 3.0 mm diameter; attitude outward.

Pedicel color: Nearest RHS 145C with a tint of RHS N187C.

Peduncle: Terete, glaucous, glabrous, typically unbranched; usually one per mature division, mostly upright to slightly arching to about 15 degrees from vertical; about 8 to 10 mm diameter at base, about 70 to 80 cm tall.

Peduncle color: Beginning nearest RHS 146D and upon maturity nearest RHS 160A.

Fruit: Non-fleshy, dehiscent, tri-loculicidal capsule; oblong ellipse; about 3.2 cm long and 5.0 mm in diameter; color as maturing nearest RHS 146D, when nearly mature and prior to dehiscence nearest RHS 150D and upon dehiscence nearest RHS 161C.

Seeds: Elliptic; with flattened wing surrounding embryo situated toward one end of ellipse; about 10 mm long, 2.5 mm wide and 1.0 mm thick at embryo; typically 6 to 24 per capsule; color nearest RHS 202A with maturity.

Disease and pest resistance: Disease or pest resistance beyond that common to *hostas* has not been observed. The plant grows best with light fertilizer, plenty of moisture and adequate drainage, but is able to tolerate some flooding and drought when mature. Hardiness at least from USDA zone 3 through 9, and other disease resistance is typical of that of other *hostas*.

The invention claimed is:

1. A new and distinct ornamental *Hosta* plant named 'Angel Falls' as herein described and illustrated.

* * * * *